(12) United States Patent
Mousset et al.

(10) Patent No.: US 6,866,151 B2
(45) Date of Patent: Mar. 15, 2005

(54) SAFETY TRANSPORT BOX FOR MEDICAL EQUIPMENT AND SPECIMENS

(75) Inventors: Patrice Mousset, Claix (FR); Jean-Pierre Bitbol, Poitiers (FR)

(73) Assignees: BENEX, Ltd., Shannon (IE); STI Plastics, Saint Romans (FR)

( * ) Notice: Subject to any disclaimer, the term of this patent is extended or adjusted under 35 U.S.C. 154(b) by 298 days.

(21) Appl. No.: 10/212,369

(22) Filed: Aug. 2, 2002

(65) Prior Publication Data

US 2004/0020814 A1 Feb. 5, 2004

(30) Foreign Application Priority Data

Aug. 6, 2001 (FR) .............................................. 01 10496

(51) Int. Cl.$^7$ .............................................. B65D 69/00
(52) U.S. Cl. ........................ 206/570; 206/438; 206/571
(58) Field of Search .......................... 190/114; 206/438, 206/563, 564, 570, 571, 572

(56) References Cited

U.S. PATENT DOCUMENTS

| | | |
|---|---|---|
| 505,222 A | 9/1893 | Hoff et al. |
| 859,817 A | 7/1907 | Kersey |
| 2,055,657 A | 9/1936 | Gordon |
| 4,194,628 A | 3/1980 | Campos |
| 4,241,833 A | 12/1980 | Luebcke |
| 4,513,866 A | 4/1985 | Thomas |
| 4,736,850 A | 4/1988 | Bowman et al. |
| 5,057,282 A * | 10/1991 | Linder .......................... 422/104 |
| 5,566,828 A | 10/1996 | Claes et al. |
| 5,653,318 A | 8/1997 | Field |
| 5,865,314 A | 2/1999 | Jacober |
| 5,934,099 A * | 8/1999 | Cook et al. ................. 62/457.2 |
| 5,979,643 A * | 11/1999 | Blonder et al. ............. 206/63.5 |
| 5,996,818 A * | 12/1999 | Boje et al. ..................... 211/74 |
| 6,116,426 A | 9/2000 | Slonim |
| 6,164,450 A | 12/2000 | Benedetti |
| 6,337,052 B1 * | 1/2002 | Rosenwasser ............... 422/102 |

FOREIGN PATENT DOCUMENTS

| | | |
|---|---|---|
| DE | 811 263 | 8/1951 |
| FR | 2 273 491 | 1/1976 |
| FR | 2 281 073 | 3/1976 |
| FR | 2 602 497 | 2/1988 |

* cited by examiner

Primary Examiner—John A. Ricci
(74) Attorney, Agent, or Firm—Gerald E. Hespos; Anthony J. Casella (57) ABSTRACT

A safety transport box is provided with an inner enclosure configured for releasably engaging specimen collection equipment. The safety transport box further includes an outer enclosure for protectively enclosing the inner enclosure. The inner and outer enclosures are spaced from one another for preventing contact related damage to the specimen collection equipment. Both the inner and outer enclosures are selectively openable for accessing the specimen collection equipment.

18 Claims, 6 Drawing Sheets

SAFETY TRANSPORT BOX FOR MEDICAL EQUIPMENT AND SPECIMENS

BACKGROUND OF THE INVENTION

1. Field of the Invention

The invention relates to a box for convenient storage and transport of medical equipment required to obtain biological specimens from a patient and to store and transport the biological specimens after collection from the patient.

2. Background of the Invention

Many medical procedures require a sample of a bodily fluid to be obtained from a patient and transported to a laboratory for analysis. For example, many medical tests require samples of blood. The samples of blood typically are drawn by using the combination of a needle assembly, a needle holder and a plurality of evacuated tubes. The needle assembly may include a needle cannula with sharply pointed proximal and distal ends and a lumen extending between the ends. A plastic hub may be securely mounted to the needle cannula at a location between the proximal and distal ends. The hub may include an array of threads or other structure for mounting the needle assembly to the needle holder. The needle assembly may further include caps and/or shields for protectively enclosing the needle cannula prior to use and, when the shield is an integrated safety feature, after use.

The needle holder typically is a tubular plastic structure with a widely open proximal end and a partly closed distal end. The distal end includes a small opening configured for releasable engagement with the hub of the needle assembly. Thus, the proximal needle will extend into the region bounded by the tubular side wall of the needle holder. The distal end of the needle cannula, however, will project distally beyond the needle holder.

The evacuated tubes typically are formed from glass in view of the ability of a glass tube to retain a vacuum. Each glass tube include a cylindrical side wall, a closed bottom and an open top. A needle pierceable stopper is affixed in the open top of the glass tube.

The above-described blood collection assemblies are employed by mounting the needle assembly to the needle holder and placing the distal end of the needle cannula into communication with the blood vessel of a patient. An evacuated tube then is urged into the open proximal end of the needle holder so that the pointed proximal end of the needle pierces the stopper of the evacuated tube to permit a flow of blood into the evacuated tube. The evacuated tube is withdrawn from the needle holder after a selected volume of blood has been collected. A second evacuated tube then may be inserted into the open proximal end of the needle holder for drawing a second sample of blood. The procedure may be repeated several times for collecting the required number of samples. The tubes with the fluid samples are marked or labeled to identify the patient and are transported to a laboratory for analysis.

Fluid samples often are collected in a hospital, and the equipment for collecting the sample may be stored on carts that can be wheeled from one location to another in the hospital. After the appropriate number of specimens have been collected, the equipment used to collect the specimens must be discarded or stored for recycling in an appropriately and safe manner. For example, exposed portions of the used needle cannula may be shielded by an integrated safety shield, separated from the needle holder and deposited in a sharps receptacle. The needle holder may be transported to a location for sterilization and recycling. Alternatively, the assembly of the needle and the needle holder may be discarded in their assembled condition and without first separating the needle from the holder. The collected fluid samples then may be placed in racks that can be transported from the location where the samples are collected to the laboratory of the hospital for analysis.

Fluid samples are not always collected in a hospital. For example, many fluid samples are collected at a doctor's office or clinic and must be transported to a laboratory for analysis. In many other instances, fluid samples are collected at the patient's residence, in an ambulance or at some other location remote from any health care facility. In these situations, the health care worker must bring the specimen collection equipment to the patient, store the collection equipment after the specimen has been collected and arranged for safe transport of the collected specimen to the laboratory.

The equipment to collect a fluid sample must be stored in a manner for convenient access by the health care worker. This storage also must prevent both breakage of the evacuated glass tubes and damage to the small fragile needles prior to use. Furthermore, specimen collection tubes must be stored in a manner that will permit safe and convenient transportation to the laboratory.

SUMMARY OF THE INVENTION

The subject invention is directed to a safety transport assembly for safe and efficient storage and transportation of equipment required to collect fluid samples from a patient and for safe and efficient transportation of the equipment and specimens to a laboratory after the samples have been collected. The assembly includes an inner enclosure and an outer enclosure. The inner enclosure has an inner base for safely storing a plurality of specimen collection containers, such as a plurality of specimen collection tubes. In one embodiment, the inner base includes a rigid peripheral frame and a top support wall formed from a resilient or elastomeric material. The top support wall may include a plurality of apertures dimensioned and configured for resilient gripping of a corresponding plurality of specimen collection containers. Thus, the specimen collection containers can be separated from the inner base merely by exerting a sufficient pulling force to overcome resilient gripping forces exerted by the resilient or elastomeric top support wall of the inner base.

The inner base may further include means for releasably retaining other equipment that may be required to collect the specimens. For example, the inner base may include means for releasably gripping a needle holder and/or at least one needle assembly. The means for gripping a needle holder may include a generally cylindrical projection dimensioned for removable insertion into the open proximal end of a needle holder. Thus, the needle holder can be separated from the inner base of the assembly merely by exerting a sufficient pulling force on the needle holder to overcome the resilient gripping forces between the needle holder and the inner base.

The assembly may further comprise an inner cover for mounting over the inner base and for enclosing the equipment stored in the inner base. The cover may include a plurality of interconnected side walls, a top wall and an open bottom that is dimensioned to engage the inner base. The side walls of the inner cover include a plurality of inner surfaces. At least one inner surface of the inner cover may be provided with an absorbing material that is capable to absorb the fluid from a tube in the event that one or more tubes break during transit. The inner cover may further include at least one hydrophobic filter extending through the wall in the inner cover. The hydrophobic filter enables an equalization of pressure across the walls of the inner cover without risk of leaking fluid from the space bounded by the inner cover. This feature can be important under any circumstance where the transport box is transported in a low pressure environment, such as in a airplane. The inner cover may further include a pattern of surface irregularities configured to provide a selected degree of rigidity for the inner cover and surface structures configured to facilitate digital manipulation of the inner cover.

The assembly further comprises an outer enclosure. The outer enclosure may include an outer base surrounding at least portions of the inner base. The outer cover may further include first and second opposed shells hingedly connected to the outer base. The shells may be of generally clam-shell construction with a front or rear wall, side walls and a top wall. The shells may be connected to the outer base for hinged rotation approximately 90° from an open position where the shells are spaced from one another to a closed position where the shells engage one another. The shells may be formed with releasable locking means for holding the shells in the closed position. Outer surface regions of the shell also may be provided with planar panels for carrying indicia to indicate, for example, the name of a laboratory or other health care provider. The inner surface of at least one shell may be configured for releasably retaining a plurality of sheets of paper or similar such flexible sheet material. The sheets may include certain medical data prepared by the health care technician or instructions on proper use of the equipment stored in the assembly.

DETAILED DESCRIPTION OF THE INVENTION

A safety transport box in accordance with the subject invention is identified generally by the numeral 10 in FIGS. 1–6. Safety transport box 10 includes an outer enclosure identified generally by the numeral 12 in FIGS. 1–6 and an inner enclosure identified generally by the numeral 14 in FIGS. 3–6.

Outer enclosure 12 is unitarily molded from a rigid thermoplastic material and includes an upwardly concave outer base 16 with a generally planar bottom wall 18, upwardly curved side walls 20 and 22, an upwardly curved front wall 24 and an upwardly curved rear wall 26. Outer enclosure 12 further includes front and rear shells 28 and 30. Front shell 28 includes a front panel 32, first and second side panels 34 and 36 and a top panel 38. Front panel 32 is connected unitarily to front wall 24 of outer base 16 along living hinge 40. Front panel 36 includes a planar region that may be imprinted with indicia to identify the source or owner of safety transport box 10. First and second parallel L-shaped ribs 42 and 44 project from the inner surface of front panel 32 and are configured for slidable receipt of printed sheet material, such as medical charts pertaining to the patient from whom the specimens will be taken or instructions for a laboratory. Top wall 40 of front shell 28 is formed with male and female latches 46 and 48.

Rear shell 30 is structurally similar to front shell 28. More particularly, rear shell 30 includes a rear panel 50, first and second side panels 52 and 54 and a top panel 56. Rear panel 50 is connected unitarily to rear wall 26 of outer base 16 along living hinge 58. Top panel 56 includes female and male latches 60 and 62 that are structurally similar to female and male latches 50 and 48 on front shell 28.

Front and rear shells 28 and 30 can be rotated hingedly about living hinges 40 and 58 and relative to outer base 16. More particularly, in an open rotational orientation, front and rear panels 32 and 50 are substantially coplanar to expose inner enclosure 14 and inner regions of outer enclosure 12. However, front and rear shells 28 and 30 can be rotated approximately 90° from the FIG. 3 open orientation into the closed orientation shown in FIGS. 1, 2 and 5. In the closed orientation, male and female latches 46 and 48 of front shell 28 releasably engage female and male latches 60 and 62 respectively of rear shell 30. Additionally in the closed condition, first side panel 34 of front shell 28 is flush with first side panel 52 of rear shell 30. Similarly, second side panel 36 of front shell 28 is flush with second side panel 54 of rear shell 30. A label may extend across the first side panels 34 and 52 or across the second side panels 36 and 54. The labels provide a tamper indication so that a user of safety transport box 10 knows immediately whether the box has been used previously.

Inner enclosure 14 includes an inner base 64 that is locked into engagement with outer base 16. Inner base 64 defines an upwardly open rectangular enclosure having a bottom wall 65 opposed first and second inner side walls 66 and 68, an inner front wall 70 and an inner rear wall 72. A peripheral flange 74 is formed unitarily with inner base 64 and extends upwardly and outwardly from first and second inner side wall 66 and 68, inner front wall 70 and inner rear wall 72. Thus, an upwardly open peripheral channel 76 extends around inner base 64. Inner base 64 is formed with arrays of radially aligned support fins 77 that extend up from bottom wall 65. Support fins 77 in each array are spaced apart sufficiently to receive the bottoms of specimen containers of different diameters.

Figure 1:
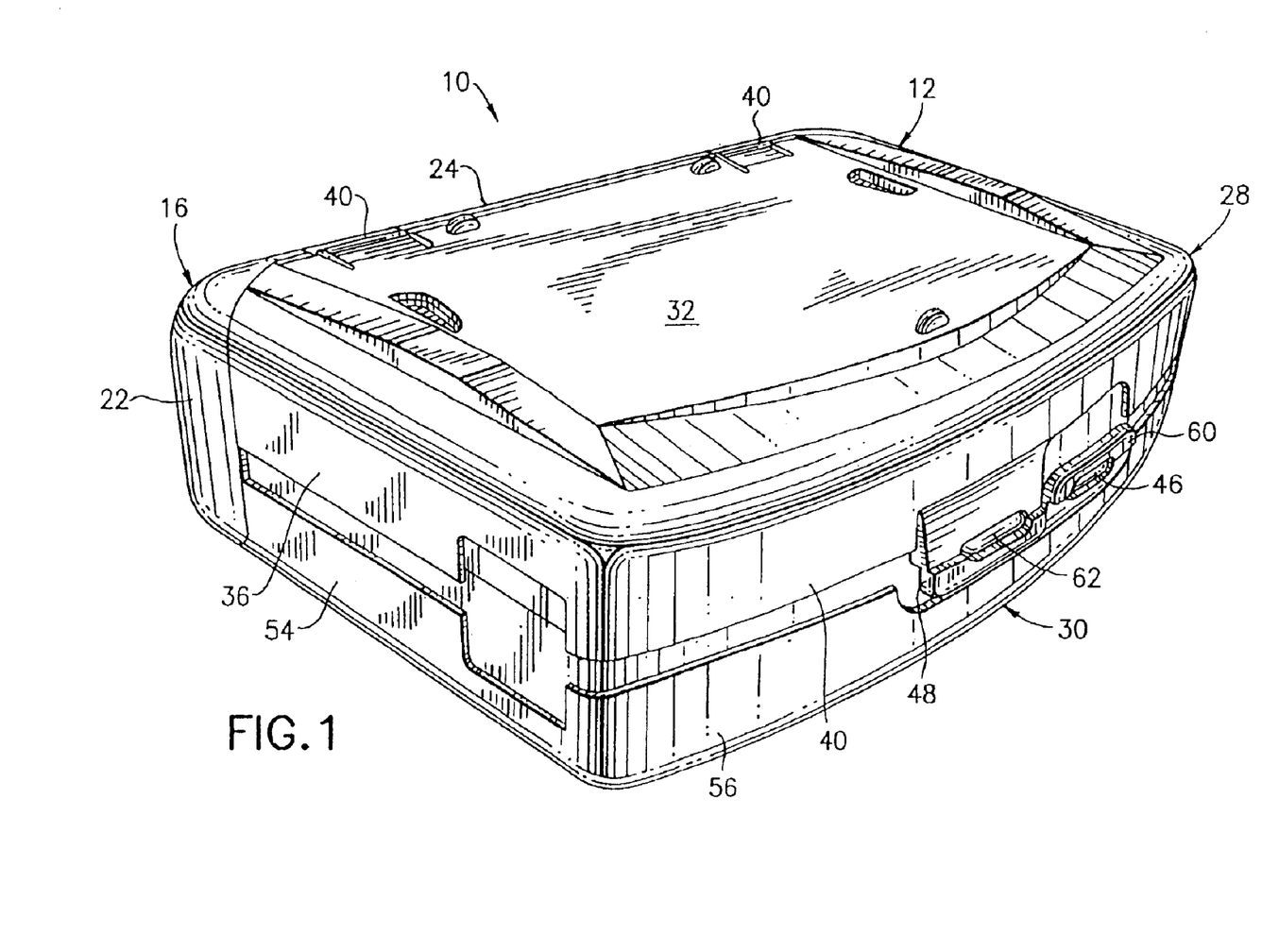
FIG. 1 is a perspective view of a safety transport box in accordance with the subject invention.
Figure 2:
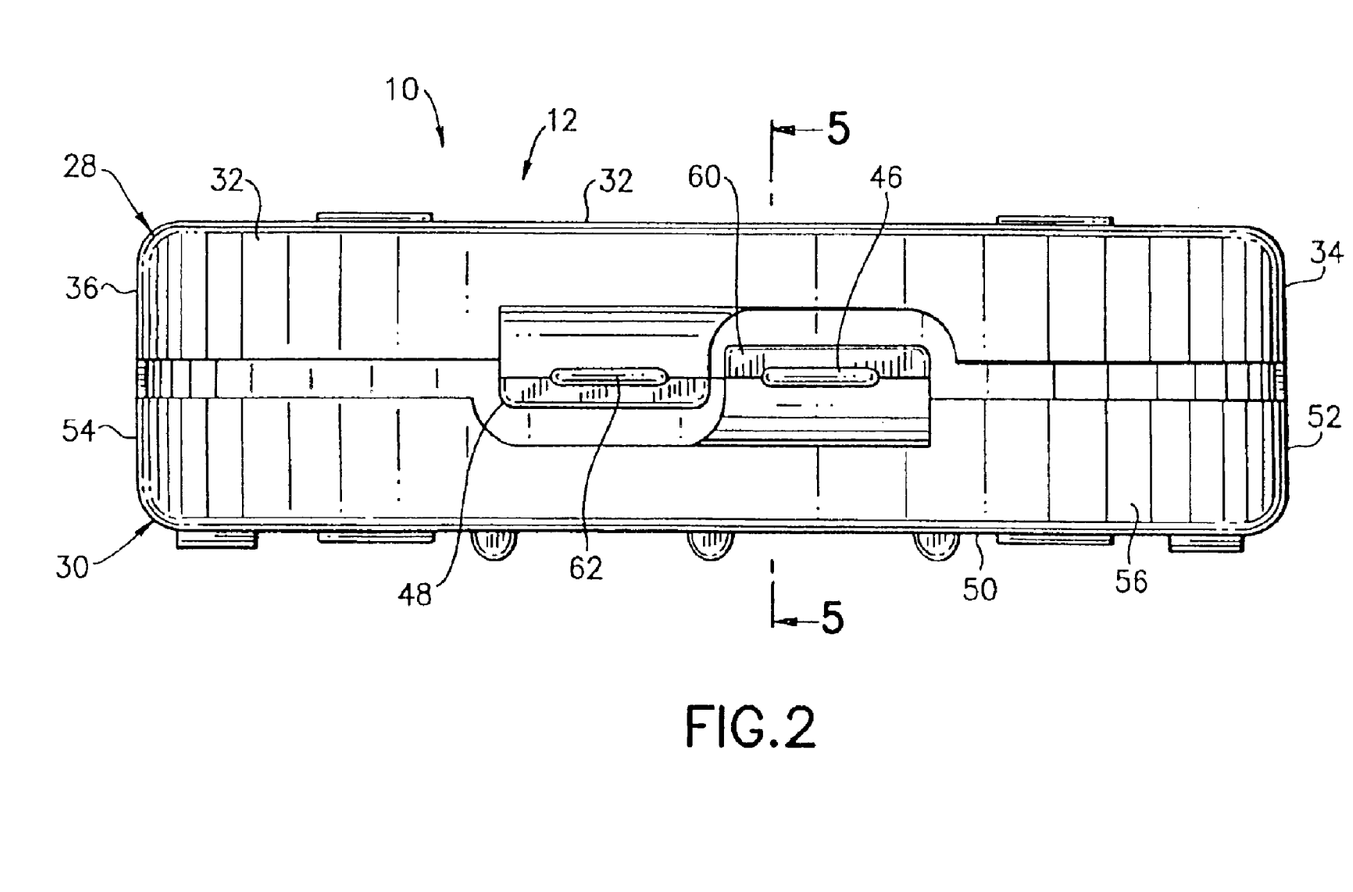
FIG. 2 is a top plan view of the closed safety transport box.
Figure 3:
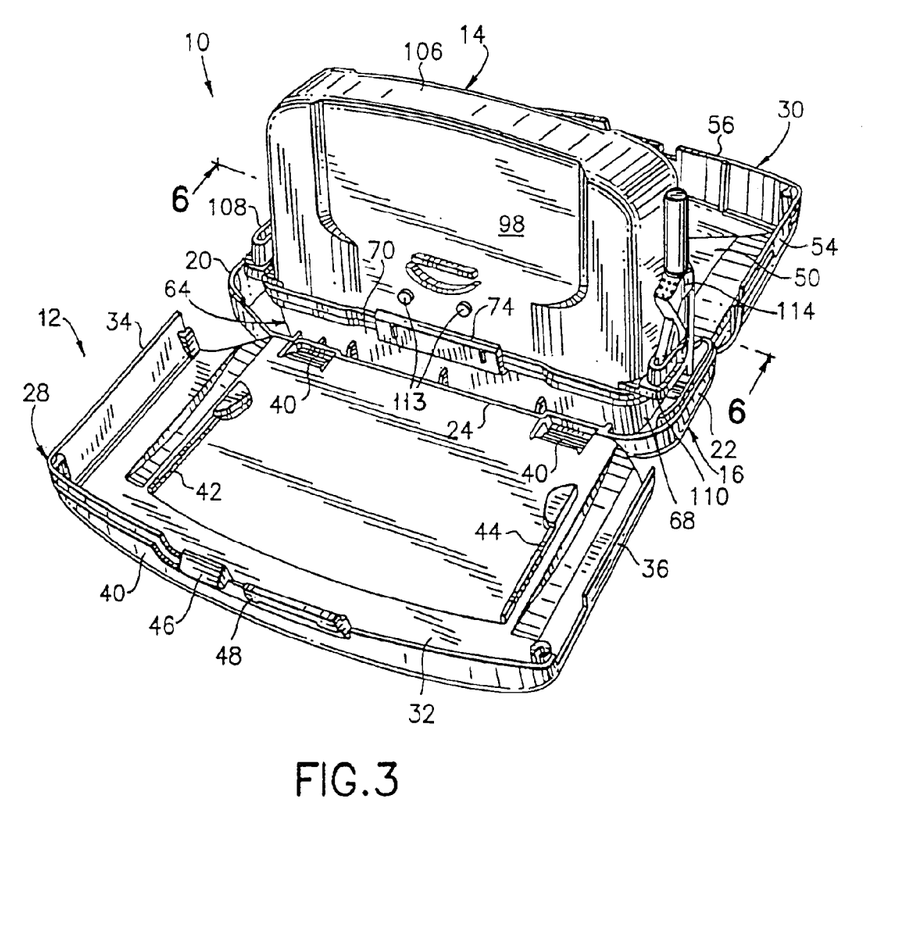
FIG. 3 is a perspective view of the safety transport box in a partly open condition and an erect orientation.
Figure 4:
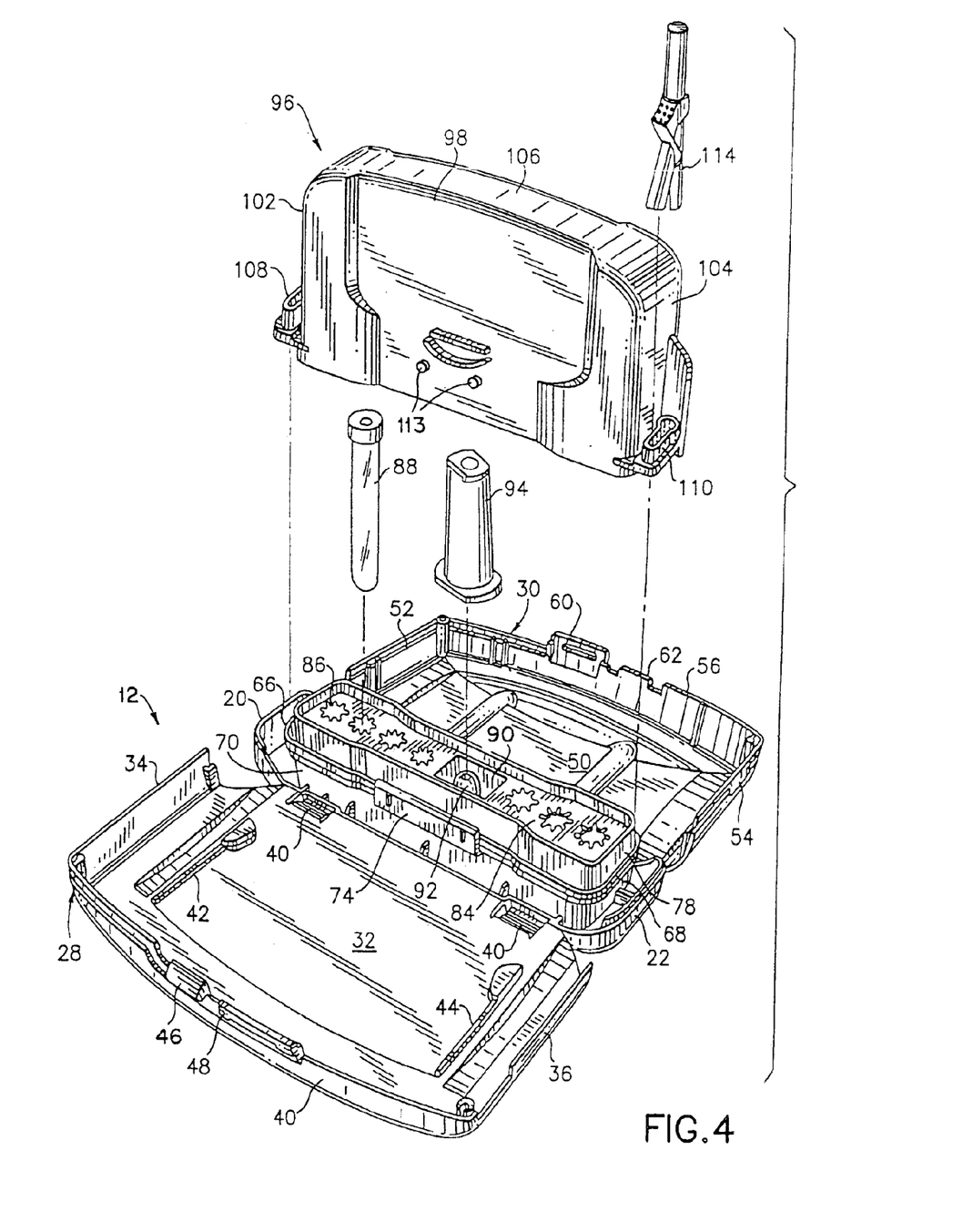
FIG. 4 is an exploded perspective view of the safety transport box in a fully open condition.
Figure 5:
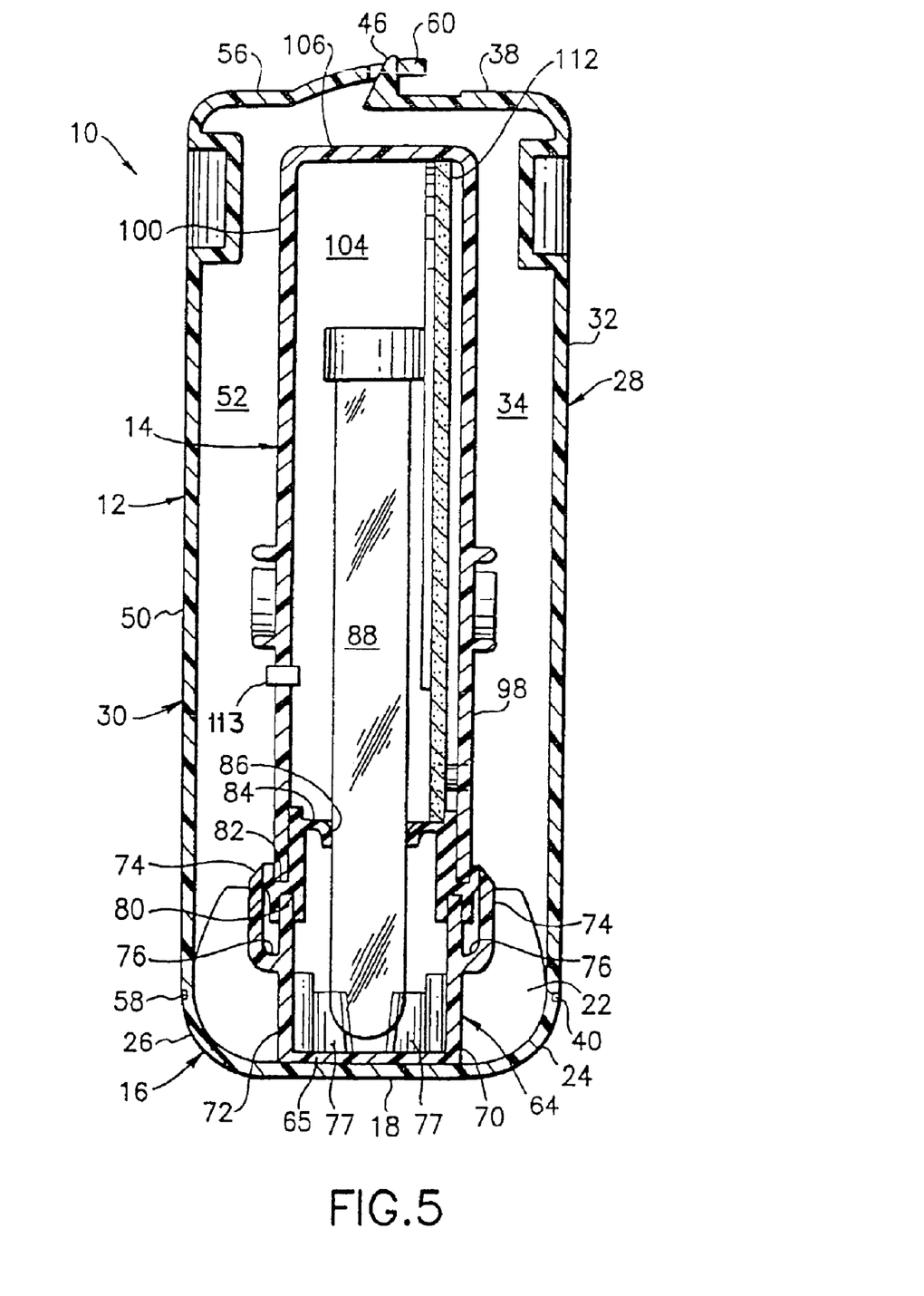
FIG. 5 is a cross-sectional view taken along line 5—5 in FIG. 2.
Figure 6:
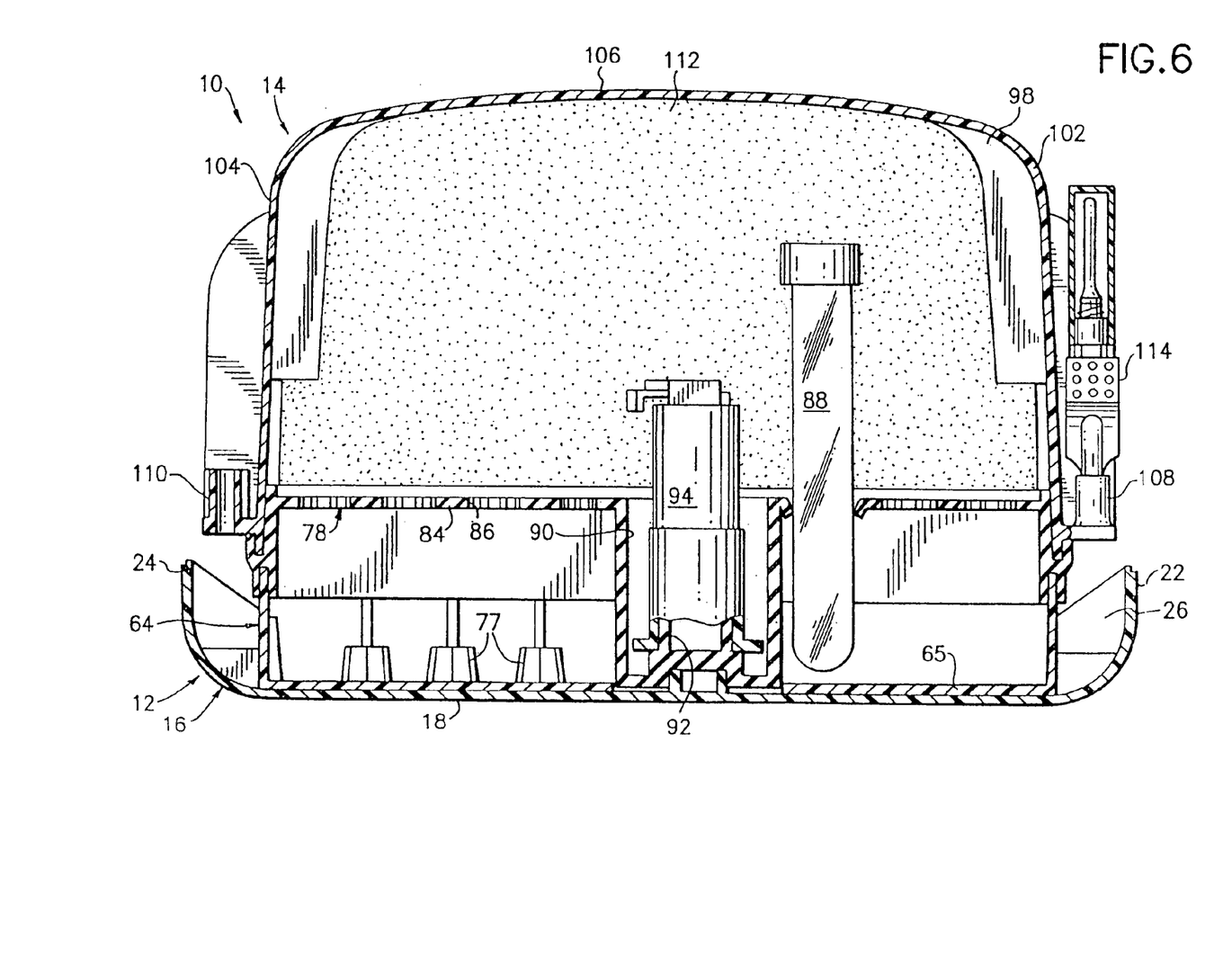
FIG. 6 is a,cross-sectional view taken along line 6—6 in FIG. 3.

Inner base 64 further includes an elastomeric support 78. The elastomeric support 78 includes a peripheral wall with a downwardly open peripheral channel 80 and an upwardly open peripheral channel 82. Downwardly open peripheral channel 80 is configured for nesting over the open top edges of inner side walls 66 and 68, inner front wall 70 and inner rear wall 72 of inner base 64. Additionally, portions of elastomeric support 78 adjacent downwardly open peripheral channel 80 nest in upwardly open peripheral channel 76 of inner base 64, as shown in FIGS. 5 and 6. Thus, a watertight seal is provided between inner base 64 and elastomeric support 78.

Elastomeric support 78 further includes a top wall 84 aligned substantially parallel to bottom wall 65 of inner base 64. Top wall 84 is formed with a plurality of apertures 86 with irregular edges dimensioned for releasable engagement of outer surfaces of a tube 88, as shown most clearly in FIGS. 4–6. The apertures 86 register with the respective arrays of radially aligned fins 77. Additionally, elastomeric support 78 is formed to include an upwardly opening rectangular recess 90 and a cylindrical projection 92 that projects upwardly in recess 90. Cylindrical projection 92 is configured for resilient and frictional engagement of interior surface regions of a needle holder 94.

Inner enclosure 14 further includes a downwardly open inner cover 96 unitarily molded from a rigid plastic. Inner cover 96 includes opposed front and rear walls 98 and 100, a first end 102, a second end wall 104 and a top wall 106. Lower edge regions of front and rear walls 90 and 100 and first and second side walls 102 and 104 are dimensioned to telescope into upwardly open peripheral channel 82 of elastomeric support 78. Thus, a watertight seal is achieved between inner cover 96 and elastomeric support 78. In this manner, inner enclosure 14 a substantially leak-proof enclosure that prevents leakage of body fluids that may have been collected and stored in inner enclosure 14, as explained further herein. Inner cover 96 is dimensioned to be spaced from front and rear shells 28 and 30 when shells 28 and 30 are in the closed condition, as shown in FIG. 5. Thus, a protective air space exists between outer enclosure 12 and inner enclosure 14. Inner cover 96 is characterized by first and second upwardly open receptacles 108 and 110 respectively formed on outer regions of first and second inner end walls 102 and 104. The receptacles 108 and 110 are configured for releasable engagement of a needle assembly, as explained further below. Inner cover 96 is characterized further by at least one sheet of absorbent material 112 internally disposed adjacent at least rear wall 100. More particularly, absorbent material 112 may be formed from cellulous fibers that will absorb material that may be released from tubes 88 in response to breakage or leakage. Absorbent material 112 functions to absorb any bodily fluid that may escape from a fluid collection tube stored therein. Such leakage might occur, for example, due to pressure differentials across the walls of the fluid collection tube or due to breakage of the tube. Inner cover 96 further includes at least one and preferably several hydrophobic filters 113 extending through walls defined by inner cover 96. Hydrophobic filters 113, by their nature, are permeable to air but impermeable to water and other liquids. Thus, hydrophobic filters 113 permit a flow of air across the walls of inner cover 96 for equalizing pressure. However, fluids, such as bodily fluids collected in tubes disposed within inner enclosure 14 will not flow through hydrophobic filters 113. This feature makes safety transport box particularly useful for environments where a pressure differential is likely to be created. For example, inner cover 96 may be sealingly engaged with elastomeric support 78 in a relatively high pressure environment. However, safety transport box then may be transported by plane or moved to a laboratory or health care facility at a higher elevation. Hydrophobic filters 113 enable an equalization of air pressure without an outward flow of bodily fluid.

Safety transport box 10 can be used to store and transport laboratory supplies and equipment that are needed to collect samples of bodily fluid, such as blood. Additionally, safety transport box 10 can be used to store certain printed material including medical reports about a particular patient, instructions for a laboratory or instructions to advise a health care technician how to use the equipment stored in safety transport box 10. Safety transport box 10 also can be used to transport specimens and used safety needle/holder assemblies for safe removal and elimination at a laboratory. For example, with reference to FIG. 4, specimen collection tubes can be engaged releasably in apertures 86 in top wall 84 of elastomeric support 78, such that the bottom of each tube 88 is nested in an array of radially aligned ribs 77. The elastomeric material from which inner support 78 is formed will cushion tube 88 from contact against safety transport box 10 during use or transportation. Similarly, a needle holder 94 can be retained frictionally on cylindrical projection 92 within rectangular recess 90 formed in elastomeric support 78. The tubes 88 and the needle holder 94 can be enclosed safely by telescoping inner cover 96 over tubes 88 and needle holder 94 and by nesting the bottom edge of top 96 in upwardly open peripheral groove 82, as shown most clearly in FIGS. 5 and 6. Shielded needle assemblies 114 then can be engaged releasably in upwardly open receptacles 108 and 110.

A health care worker can use safety transport box 10 by carrying box 10 to a patient who requires blood or other bodily fluids to be collected and tested by a laboratory. The technician places bottom wall 18 of outer base 16 on a table or other supporting surface. Latches 46, 48, 60 and 62 are manipulated to permit front and rear shells 28 and 30 to be rotated away from one another and into the orientation shown in FIG. 3. The health care technician then grips inner cover 96 and pulls upwardly to separate inner cover 96 from open peripheral channel 82 in elastomeric support 78 of inner base 64. The open bottom edges of inner cover 96 then can be supported on a table or other planar surface near outer enclosure 12. The health care worker then removes needle holder 94 from cylindrical projection 92 and removes the shielded needle assembly 114 from one of the receptacles 108 and 110 in inner cover 96. Needle assembly 114 then is engaged with needle holder 94 in the conventional manner. This typically requires removing a proximal cap from a proximal needle on needle assembly 114 and engaging a hub of needle assembly 114 in a mounting aperture of needle holder 94. A distal cap on needle assembly 114 then may be removed and the health care worker may position the distal tip of the needle cannula into a targeted blood vessel of the patient. The health care worker then sequentially removes evacuated blood collection tubes 88 from inner base 64 merely by pulling tubes 88 upwardly with sufficient force to separate tubes 88 from apertures 86 in top wall 84 of elastomeric support 78. A selected volume of blood or other bodily fluid is collected in each of a plurality of tubes 88, and tubes 88 are sequentially redeposited into apertures 86 of elastomeric support 78. After a sufficient number of tubes 88 have been collected for the required tests, needle holder 94 and needle assembly 114 are withdrawn from the patient. Needle assembly 114 is safely shielded and then may be separated from needle holder 94 or may be re-deposited attached with the holder in an upright position over cylindrical projection 92. When separated from the needle assembly 114, needle holder 94 may be positioned again on cylindrical projection 92 in inner base and the shielded needle assembly can be discarded in a safe manner. Inner cover 96 then can be secured over inner base 64 by telescoping inner cover 96 over tubes 88 and needle holder 94 or needle/holder assembly with safety feature engaged and telescoping inner cover the bottom edges of inner cover 96 into upwardly open channel 82 in elastomeric support 78 of inner base 64. The health care worker then merely rotates front and rear shells 28 and 30 toward one another and into the closed condition shown in FIGS. 2 and 5. The safety transport box then can be transported safely to a laboratory for analysis of the collected specimens and for needle/holder assembly elimination.

The illustrated embodiment shows the safety transport box 10 adapted for storing and transporting equipment to collect samples of blood. However, the safety transport box 10 can be used for collecting other bodily fluids, such as urine, saliva and such. These optional embodiments do not require the inner enclosure to be adapted for storing a needle holder or needle assembly.

What is claimed is:

1. A safety transport box comprising: an inner enclosure having an inner base and an inner cover removably mounted to said inner base, said inner base including support means for removably mounting specimen collection equipment, said inner base comprising a side wall enclosure formed from a rigid material and an elastomeric support for providing a watertight sealing between said inner base and said inner cover and for resiliently supporting said specimen collection equipment, said safety transport box further comprising an outer enclosure protectively surrounding said inner enclosure, said outer enclosure including at least one outer cover for selectively opening said outer enclosure and accessing said inner enclosure.

2. The safety transport box of claim 1, wherein the said elastomeric support further comprises at least one opening configured and dimensioned for resiliently engaging said specimen collection equipment.

3. The safety transport box of claim 2, wherein said elastomeric support further comprises a projection for telescoped engagement with an element of said specimen collection equipment having an open tubular configuration.

4. A safety transport box comprising: an inner enclosure having an inner base and an inner cover removably mounted to said inner base, said inner base including support means for removably mounting specimen collection equipment, said safety transport box further comprising an outer enclosure protectively surrounding said inner enclosure, said outer enclosure including at least one outer cover for selectively opening said outer enclosure and accessing said inner enclosure, the inner enclosure further comprising at least one hydrophobic filter extending through said inner enclosure to permit equalization of air pressure between said inner enclosure and said outer enclosure while preventing leakage of fluid from said inner enclosure to said outer enclosure.

5. The safety transport box of claim 4, wherein said inner cover includes a side wall enclosure, a closed top and an open bottom, said inner cover being configured for telescoped substantially waterproof engagement with said inner base.

6. The safety transport box of claim 5, wherein said inner cover comprises a plurality of inner surfaces, at least one of said inner surfaces having an absorbent layer for absorbing fluid spilled in said inner enclosure.

7. The safety transport box of claim 6, where said inner cover includes at least one receptacle configured for releasably engaging a needle assembly.

8. A safety transport box comprising: an inner enclosure having an inner base and an inner cover removably mounted to said inner base, said inner base including support means for removably mounting specimen collection equipment, said safety transport box further comprising an outer enclosure protectively surrounding said inner enclosure, said outer enclosure including an outer base and at least one outer cover for selectively opening said outer enclosure and accessing said inner enclosure, said inner base is being formed unitarily with said outer base.

9. A safety transport box comprising: an inner enclosure having an inner base and an inner cover removably mounted to said inner base, said inner base including support means for removably mounting specimen collection equipment, said safety transport box further comprising an outer enclosure protectively surrounding said inner enclosure, said outer enclosure including an outer base and at least one outer cover for selectively opening said outer enclosure and accessing said inner enclosure, said outer cover including front and rear outer shells hingedly connected to said outer base and selectively closeable around said inner enclosure.

10. The safety transport box of claim 9, wherein said front and rear outer shells are formed unitarily with said outer base.

11. The safety transport box of claim 9, wherein said front and rear outer shells include locking means for releasably locking said front and rear outer shells around said inner enclosure.

12. The safety transport box of claim 9, wherein said front and rear outer shells include inner surfaces, the inner surface of at least one of said front and rear shells being formed with at least one channel for releasably receiving sheet material.

13. A safety transport box comprising an inner base with an upwardly open rigid side wall, an elastomeric support mounted to said side wall of said inner base, said elastomeric support including at least one opening for releasably engaging a specimen collection container; an inner cover having a plurality of interconnected side walls, a top wall and an open bottom, said inner cover being releasably mounted to said inner base for selectively enclosing and protecting a specimen collection container engaged by said elastomeric support; at least one hydrophobic filter mounted in and extending through said inner cover for substantially equalizing pressure across said inner cover; an upwardly concave outer base engaged With said inner base, front and rear shells hinged to said outer base and rotatable relative to said outer base from an open position where said inner cover and said inner base are accessible and a closed position where said front and rear shells are in surrounding spaced relationship to said inner cover.

14. The safety transport box of claim 13, wherein said elastomeric support is configured for watertight engagement with both said inner base and said inner cover for preventing leakage of specimens supported between said inner cover and said inner base.

15. The safety transport box of claim 13, wherein said front and rear shells are unitary with said outer base.

16. The safety transport box of claim 13, wherein said inner and outer base, said front and rear shells and said inner cover are formed from a rigid thermoplastic material.

17. The safety transport box of claim 13, wherein said inner cover further comprises means for releasably engaging a needle assembly.

18. The safety transport box of claim 13, wherein said elastomeric support comprises a support projection for releasably engaging a generally tubular needle holder.

* * * * *